(12) United States Patent
Carolus et al.

(10) Patent No.: US 11,037,660 B2
(45) Date of Patent: Jun. 15, 2021

(54) COMMUNICATION SYSTEM FOR DYNAMIC CHECKLISTS TO SUPPORT RADIOLOGY REPORTING

(71) Applicant: KONINKLIJKE PHILIPS N.V., Eindhoven (NL)

(72) Inventors: Heike Carolus, Hamburg (DE); Juergen Weese, Norderstedt (DE); Yuechen Qian, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 841 days.

(21) Appl. No.: 15/547,647

(22) PCT Filed: Jan. 22, 2016

(86) PCT No.: PCT/IB2016/050309
§ 371 (c)(1),
(2) Date: Jul. 31, 2017

(87) PCT Pub. No.: WO2016/125039
PCT Pub. Date: Aug. 11, 2016

(65) Prior Publication Data
US 2018/0358121 A1 Dec. 13, 2018

Related U.S. Application Data

(60) Provisional application No. 62/112,185, filed on Feb. 5, 2015.

(51) Int. Cl.
*G16H 10/60* (2018.01)
*G16H 15/00* (2018.01)
(Continued)

(52) U.S. Cl.
CPC .............. *G16H 10/60* (2018.01); *G06Q 10/10* (2013.01); *G16H 15/00* (2018.01); *G16H 30/20* (2018.01); *G16H 30/40* (2018.01)

(58) Field of Classification Search
CPC ........ G16H 10/60; G16H 15/00; G16H 30/20; G16H 40/67; G16H 80/00; G16H 40/63;
(Continued)

(56) References Cited

U.S. PATENT DOCUMENTS 7,437,659 B2  10/2008  Taniwaki
7,617,461 B2  11/2009  Yoshida
(Continued)

FOREIGN PATENT DOCUMENTS

JP  2006260318  9/2006
JP  2009078050  4/2009
(Continued)

OTHER PUBLICATIONS

Measuring the Impact of Technology on Nurse Workflow: A Mixed Methods Approach, Cady, Rhonda Guse. University of Minnesota, ProQuest Dissertations Publishing, 2012 (Year: 2012).*

*Primary Examiner* — Joseph D Burgess (57) ABSTRACT

A radiology workstation (20) includes a display device (22), at least one user input device (24, 26, 28), and an electronic data processor. The workstation provides an image rendering component (30) for rendering a radiological image, and a report data entry component (32) for entry of a radiology examination report (34) via the at least one user input device and for display of the radiology examination report during entry. The workstation further provides a dynamic checklist component (40) for storing a queue (44) of open checklist items, and for: displaying a checklist comprising open checklist items stored in the queue; dynamically analyzing the radiology examination report during entry to identify a checklist update trigger; updating the queue of open checklist items based on the identified checklist update trigger; and updating the display of the checklist to comprise the open checklist items stored in the updated queue.

17 Claims, 4 Drawing Sheets

(51) Int. Cl.
*G06Q 10/10* (2012.01)
*G16H 30/40* (2018.01)
*G16H 30/20* (2018.01)

(58) Field of Classification Search
CPC ........ G16H 30/40; G16H 10/00; G16H 30/00;
G06Q 50/22; G06Q 50/24; G06Q 10/06;
G06Q 10/063114; G06Q 10/10; G06Q
10/109; G06Q 10/06316; G06Q 10/063;
G06Q 10/06311; G06Q 10/063116; G06Q
10/0633; G06Q 10/1095; G06Q 10/1097;
G06F 19/321; G06F 40/169; G06F 19/30;
G06F 9/542; A61B 5/7425; A61B 5/743;
A61B 5/0013; A61B 6/032; A61B 6/03
See application file for complete search history.

(56) References Cited

U.S. PATENT DOCUMENTS

| | | | |
|---|---|---|---|
| 7,693,727 | B2 | 4/2010 | Moore |
| 2004/0039623 | A1* | 2/2004 | Setteducati ............ G06Q 10/10 705/7.24 |
| 2006/0074720 | A1 | 4/2006 | Brutting et al. |
| 2006/0277073 | A1* | 12/2006 | Heilbrunn ............... G06Q 50/24 705/3 |
| 2009/0287487 | A1* | 11/2009 | Rossman ............... G06F 19/321 704/235 |
| 2010/0138239 | A1* | 6/2010 | Reicher ............... G06F 21/6245 705/3 |
| 2012/0316874 | A1* | 12/2012 | Lipman ................ G16H 15/00 704/235 |
| 2013/0124527 | A1* | 5/2013 | Lee ........................ G16H 50/70 707/737 |
| 2014/0006926 | A1 | 1/2014 | Yeluri et al. |
| 2014/0006943 | A1 | 1/2014 | Robbins et al. |
| 2014/0278448 | A1 | 9/2014 | Sadeghi et al. |
| 2014/0324423 | A1* | 10/2014 | Koll ....................... G06F 3/167 704/235 |

FOREIGN PATENT DOCUMENTS

| | | |
|---|---|---|
| JP | 2009093568 | 4/2009 |
| JP | 2011145935 | 7/2011 |
| WO | 2014205079 A2 | 12/2014 |

* cited by examiner

COMMUNICATION SYSTEM FOR DYNAMIC CHECKLISTS TO SUPPORT RADIOLOGY REPORTING

CROSS-REFERENCE TO PRIOR APPLICATIONS

This application is the U.S. National Phase application under 35 U.S.C. § 371 of International Application No. PCT/M2016/050309, filed on Jan. 22, 2016, which claims the benefit of U.S. Provisional Application No. 61/112,185, filed on Feb. 5, 2015. These applications are hereby incorporated by reference herein.

The following relates generally to medical workflow systems, radiology reporting systems, medical data integration systems, and related arts.

Medical imaging is a specialized area employing specialized equipment, which also typically employs dedicated specialist personnel. In a typical radiology workflow, a physician orders a radiology examination based on a physical examination off the patient and any available laboratory test results. The examination is scheduled and performed by a radiologic technologist, and the images are (optionally) printed and are stored electronically on an electronic data archiving system such as a dedicated Picture Archiving and Communication System (PACS). Thereafter, a radiologist reads (i.e. interprets) the images in accord with the ordered examination. In reviewing the images, the radiologist may take into account other available information such as patient medical history, physical examination records, hematology, biopsy, or other test results, any previous imaging examination(s), or so forth. The radiologist may make a medical diagnosis based on the images and the additional available information. The radiologist prepares a written radiology report that is forwarded to the physician who ordered the radiology examination for consideration, along with other available information, in diagnosing the patient and designing a treatment regimen.

In the foregoing process, the radiologist reads the images using a dedicated software program running on a computer (sometimes called a "workstation") with a high resolution graphical user interface (GUI) for displaying radiological images. One such system is the IntelliSpace PACS radiology reading solution available from Koninklijke Philips N.V. (Eindhoven, the Netherlands). The IntelliSpace PACS workstation provides a GUI for rendering radiological images, entering the radiology examination report, and can also present results of previous radiology examinations. The workstation typically also provides access to an Electronic Medical Record (EMR) archive system which stores patient records such as medical history, physical examination reports, and laboratory results. This allows the radiologist to review patient medical data other than radiological data. By contrast, radiology examination results comprise specialized imaging information, and are typically stored in the PACS, with the EMR storing at most an abbreviated reporting such as radiology report and possibly one or two representative images (often at lower resolution and/or compressed).

The present application provides a new and improved system and method which overcome these problems and others.

In accordance with one aspect, a radiology workstation comprises: an image rendering component including a display device and an electronic data processor programmed to render a radiological image on the display device; a radiology examination report data entry component including the display device, at least one user input device, and the electronic data processor programmed for entry of a radiology examination report via the at least one user input device and display of the radiology examination report on the display device during entry; and a dynamic checklist component including the display device, a storage medium storing a queue of open checklist items, and the electronic data processor. In implementing the dynamic checklist component, the electronic data processor is programmed to: display a checklist on the display device comprising open checklist items stored in the queue; dynamically analyze the radiology examination report during entry to identify a checklist update trigger; update the queue of open checklist items based on the identified checklist update trigger; and update the display of the checklist on the display device to comprise the open checklist items stored in the updated queue.

In accordance with another aspect, a radiology examination report generation method comprises: rendering a radiological image on a display device; receiving entry of a radiology examination report via at least one user input device; displaying the radiology examination report on the display device during entry; displaying a checklist on the display device comprising open checklist items stored in a queue; dynamically analyzing the radiology examination report during entry to identify a checklist update trigger; updating the queue of open checklist items based on the identified checklist update trigger; and updating the display of the checklist on the display device to comprise the open checklist items stored in the updated queue.

In accordance with another aspect, a non-transitory storage medium stores instructions executable by an electronic data processor to perform a radiology examination report generation method comprising: rendering a radiological image on a display device in a first window; receiving entry of a radiology examination report via at least one user input device; displaying the radiology examination report on the display device in a second window during entry; displaying a checklist on the display device in a third window that is different from the second window wherein the checklist comprises open checklist items stored in a queue; dynamically analyzing the radiology examination report during entry to identify a checklist update trigger; updating the queue of open checklist items based on the identified checklist update trigger; and updating the display of the checklist on the display device in the third window to comprise the open checklist items stored in the updated queue.

One advantage resides in providing a radiology workstation with an improved user interface that increases efficiency and effectiveness of the radiology reading process by providing contextual guidance as the radiologist drafts the radiology examination report, without constraining the radiologist to a pre-defined structured examination report form.

Another advantage resides in providing a radiology workstation with improved communication with an Electronic Medical Record (EMR) archive so as to increase efficiency and effectiveness of the radiology reading process, without suffering the disadvantage of directly entering information from the EMR into the radiology examination report authored by the radiologist.

A more general advantage resides in providing a radiology workstation with an improved user interface and improved communication with outside systems, especially the EMR, so as to increase efficiency and effectiveness of the radiology reading process.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Radiological diagnosis and reporting is a highly specialized task that requires the radiologist to synthesize diverse information. The reading of the radiological images is itself a complex and sometimes subjective process. Depending upon the primary findings generated by the initial reading, the radiologist may be expected to further interpret the radiological images to draw secondary findings. For example, if the primary finding is detection of a tumor in a lymph node, then a secondary finding may be the lymph node status. While the radiological images are naturally of central importance, the radiologist also considers other available information such as other laboratory test results, physical examination reports, and so forth that may either support or controvert the preliminary diagnosis or other medical conclusions drawn by reading the images.

Existing radiology workstations have certain deficiencies recognized herein. Although the workstation provides the tools to enable the radiologist to perform the reading, the workstation provides limited guidance in performing the complex radiology images reading process. One approach to provide such guidance is to use structured radiology examination report forms, for example by providing freeform text entry fields with headings that indicate the type of information to include in each field. A more aggressive structured report form employs constrained user dialog fields, such as drop-down selection lists or a set of options with selectable radio buttons, check boxes, or the like, which limit the radiologist to the available selection options. Use of a standardized structured report form for a given type of radiology examination advantageously improves run-to-run uniformity, and provides guidance to the radiologist. However, the radiologist may be uncomfortable with being constrained to the limited options provided by a standardized structured report form, and in some cases the patient's condition may not fit into any particular structured report form.

A related deficiency in existing radiology workstations is poor communication with outside archival systems, especially the Electronic Medical Record (EMR) archive which stores most non-radiological patient medical information. Typically, the radiology workstation provides an EMR interface operating in parallel with the radiology reading software, for example implemented as a separate program or as a distinct EMR component of the radiology reading program accessed via a dedicated EMR GUI window. While this provides the radiologist with access to the EMR content, it provides no guidance to the radiologist as to what information contained in the EMR is relevant to the particular radiology examination in progress. Requiring the radiologist to navigate the EMR separately from operating the image reading software is also mentally taxing and labor-intensive as the radiologist must recognize (based on education/ training) that a given piece of information is contained in the EMR and is of use in the radiology examination, and then must use the EMR component to navigate through the EMR to locate and retrieve that piece of information. A partial solution, operating in conjunction with a structured radiology examination report form, might be to automatically populate structured fields of the report form with information automatically retrieved from the EMR; however, in addition to requiring the use of a structured report form with its aforementioned deficiencies, this approach creates a situation in which the radiologist's report includes information not actually entered by the radiologist. Again, the radiologist may be uncomfortable with such a situation.

Thus, existing radiology workstations have technical problems including inefficient and sometimes ineffective user interfaces, and inefficient and sometimes ineffective communication with outside systems, especially the EMR archive. Existing solutions for these technical problems, such as providing a radiology examination report data entry system employing a structured radiology examination report form, and automatic population of fields of such a form from the EMR archive, have certain deficiencies at least including those noted above.

These technical problems are addressed in embodiments disclosed herein by providing a radiology workstation with an image rendering component, a radiology examination report data entry component, and further including a dynamic checklist component that is separate from the radiology examination report data entry component but that is advantageously in communication with the radiology examination report data entry component in order to display checklist items that are dynamically selected during drafting of the radiology examination report using the radiology examination report data entry component based on the dynamically changing content of the report. This solution improves efficiency of the radiology workstation by providing contextual guidance as the radiologist drafts the radiology examination report and yet it does not suffer the disadvantage of constraining the radiologist to a pre-defined structured examination report form. In some embodiments, the dynamic checklist component is configured to automatically populate checklist items with information retrieved from the EMR archive. This solution improves communication with the EMR archive, but does not suffer the disadvantage of directly entering information from the EMR into the radiology examination report authored by the radiologist.

Figure 1:
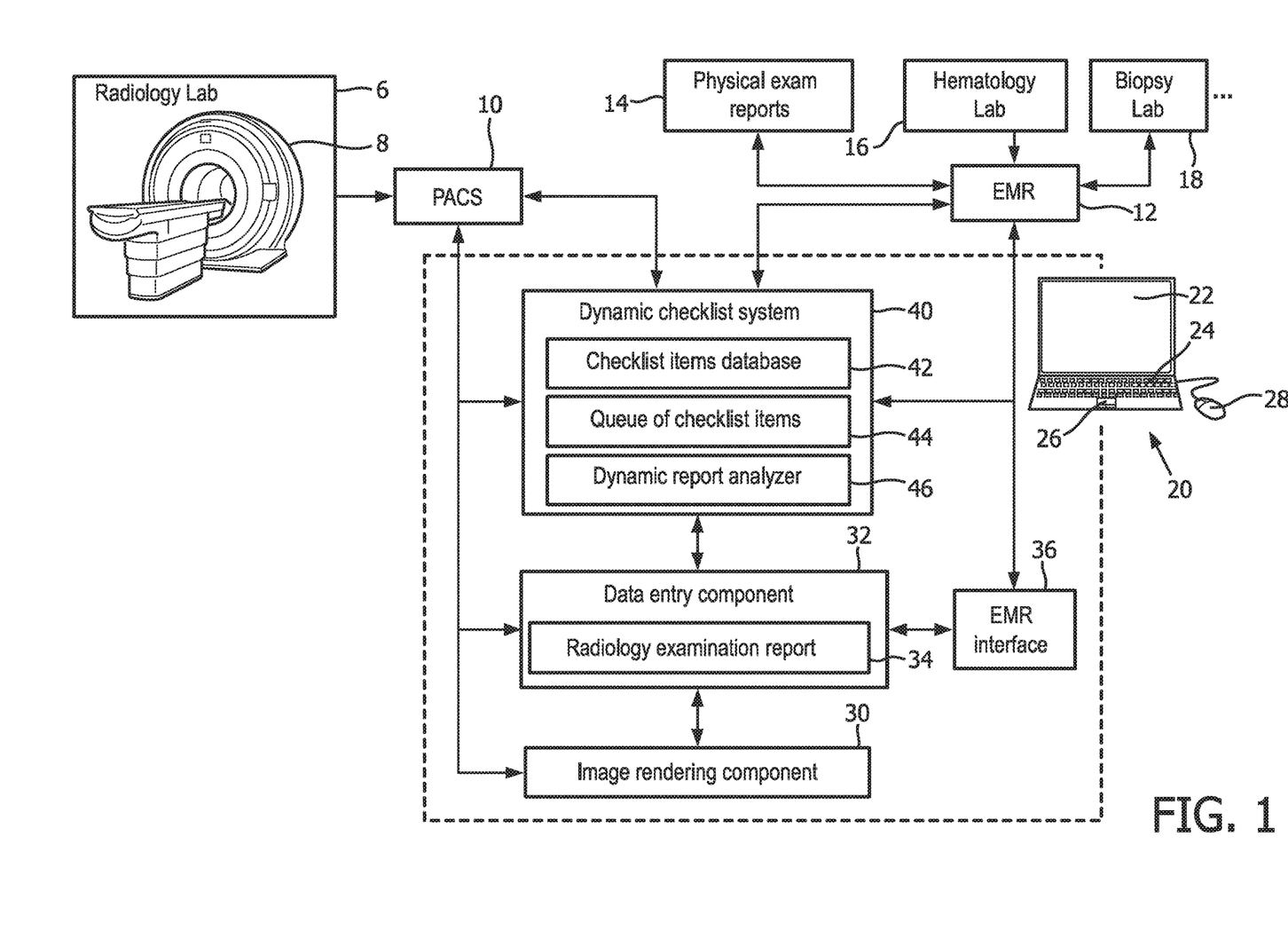
FIG. 1 diagrammatically shows a radiology workstation.

With reference to FIG. 1, a radiology workflow includes a radiology lab 6 at which a radiologic technologist or other medical personnel acquires radiological images of a subject (e.g. in-patient or out-patient) using a medical imaging system 8. By way of some illustrative non-limiting examples, the medical imaging system 8 may comprise a magnetic resonance (MR) imaging scanner, a transmission computed tomography (CT) imaging scanner, a positron emission tomography (PET) imaging scanner, a gamma camera used to perform single photon emission computed tomography (SPECT) imaging, an ultrasound imaging system, a planar transmission x-ray imaging system, various combinations thereof (such as a CT/PET, CT/SPECT, MR/PET or other hybrid imaging scanner), or so forth. Some suitable commercial embodiments of such imaging systems and scanners are available from Koninklijke Philips N.V. (Eindhoven, the Netherlands). The acquired radiological images are suitably stored in a dedicated radiology storage system such as an illustrative Picture Archiving and Communication System (PACS) 10, although storage in another data system is contemplated, such as storage in an illustrative Electronic Medical Record (EMR) 12 which provides general-purpose storage for medical records including physical examination reports 14, hematology lab results 16, biopsy lab results 18, and so forth.

At some time after the radiology laboratory session, a radiologist reads (that is, interprets) the radiological images and prepares a radiology examination report using a radiology computer (i.e. workstation) 20 that includes a high resolution display device 22 (where "high resolution" is to be understood to be sufficiently high resolution to provide sufficient imaging detail to perform a reading of the images) and at least one user input device, such as an illustrative keyboard 24 and a track pad 26, mouse 28, or other pointing device, although additional or other user interface device(s) are contemplated, such as a touch-screen component of the display device 22. The workstation 20 further includes an electronic data processor. The processor is not shown in FIG. 1, but typically comprises an integrated circuit (IC) or set of IC's mounted on a motherboard having circuitry interconnecting with random access memory (RAM), read only memory (ROM), and/or other ancillary components, disposed inside the housing of the workstation 20. Additionally or alternatively, the electronic data processor of the workstation 20 may comprise a remote processor, for example a remote server computer in operative communication with the workstation 20 via an electronic data network such as a wired or wireless local area network (LAN), the Internet, various combinations thereof, or so forth. The electronic data processor of the workstation 20 executes software that together with the user interfacing components 22, 24, 26, 28 performs various tasks related to the radiology reading. In the embodiment of illustrative FIG. 1, an image rendering component 30 comprises the electronic data processor programmed to render a radiological image retrieved from the PACS 10 on the display device 22.

A radiology examination report data entry component 32 comprises the electronic data processor programmed for entry of a radiology examination report 34 via the at least one user input device 24, 26, 28 and display of the radiology examination report on the display device 22 during entry. In some embodiments the radiology examination report data entry component 32 provides a "what-you-see-is-what-you-get", i.e. WYSIWYG, graphical user interface (GUI) in which the radiation examination report 34 is displayed in its final format and the radiologist can, for example, use a pointing device 26, 28 to select and drag-and-drop an image displayed in a rendering GUI window by the image rendering component 30 over to a report GUI window in which the radiology examination report data entry component 32 displays the radiology examination report 34 during entry. (In an alternative approach, the radiologist may right-click on the image using the mouse 28 to bring up a contextual menu allowing the image to be copied to an internal "clip board", and then the radiologist performs a "paste" operation to copy the image into the report.)

An Electronic Medical Record (EMR) interface 36 comprises the electronic data processor programmed to enable the radiologist to navigate the EMR archive 12 to retrieve medical information regarding the subject of the radiology examination (and, optionally, to retrieve records of other patients, for example to allow the radiologist to compare the current case with a previous case). As with interaction with the rendered radiological images, in some embodiments the radiologist can transfer information from the EMR 12 to the radiology report by performing a drag-and-drop or copy-and-paste operation using the pointing device 26, 28, or a touch-screen display or so forth.

The radiologist who uses the radiology workstation 20 to read radiology images and draft the radiology examination report 34 is expected to be a person with medical training (e.g., a physician, doctor, or the like) including specialized radiology training, that is, specialized training in interpreting (reading) radiology images. The radiologist may be employed only to perform such readings, or the radiologist may be a medical specialist (e.g. orthopedic specialist) who has the requisite radiology training to be competent in reading radiology images (at least of a certain type). Operation of the image rendering component 30 also requires the radiologist to have familiarity with the PACS system 10 sufficient to navigate to find and retrieve an image; similarly, operation of the EMR interface 36 requires the radiologist to have familiarity with the EMR archive 12 sufficient to navigate to find and retrieve patient data of interest. However, in practice the radiologist may have limited knowledge of the EMR archive 12, since it stores patient data in numerous areas that go beyond the confines of radiology (e.g. blood work produced by the hematology lab 16, biopsy results from the biopsy lab 18, and so forth). The radiologist may not know whether laboratory test results of interest are available for the subject, or may be unfamiliar with the data structures used to store those results in the EMR archive 12.

Moreover, while the radiologist has specialized radiology training, the process of reading radiology images is complex. The reading depends on numerous factors such as the type or types of images (MR images versus CT images, for example), the medical condition under examination, any relevant secondary conditions, patient characteristics (age, gender, ethnicity, et cetera), any specifics specified by the patient's physician in the radiology examination order, and so forth. Thus, it would be useful to provide the radiologist with some guidance specific to the particular radiology reading being performed. .

With continuing reference to FIG. 1, to this end a dynamic checklist system 40 comprises the electronic data processor of the workstation 20 programmed to perform operations such as displaying a checklist on the display device 22 comprising open checklist items selected from a checklist items database 42 and stored in a queue 44 of open checklist items, dynamically analyzing the radiology examination report 34 during entry by the data entry component 32 to identify a checklist update trigger, updating the queue 44 of open checklist items to add one or more checklist items from the checklist items database 42 based on the identified checklist update trigger, and updating the display of the checklist on the display device 22 to comprise the open checklist items stored in the updated queue 44. The queue 44 may be stored on any non-transitory storage medium (not shown) for which the electronic data processor has read/write access, such as in random access memory (RAM), a hard disk drive, a writable optical disk, or so forth. In the illustrative embodiment, the dynamic analysis of the radiology examination report 34 to identify a checklist update trigger is performed by a dynamic report analyzer component 46 using natural language processing (NLP) and/or keyword-based searching implemented by suitable programming of the electronic data processor of the workstation 20. If the radiology examination report data entry component 32 employs a standardized structured report form, then it is contemplated for the dynamic checklist system 40 to leverage a priori knowledge of the report form layout to identify checklist update triggers for example, if the report form includes dropdown list dialog field via which the radiologist enters the imaging modality (MR, CT, ultrasound, et cetera) then the dynamic checklist system 40 may be programmed to directly read this field. However, the radiology examination report 34 entered/edited using the data entry component 32 preferably includes at least some freeform data entry fields to provide unconstrained input capability, and in some embodiments the examination report 34 may not include any constrained user dialog fields. The NLP and/or keyword based dynamic report analyzer component 42 advantageously allows for dynamic analysis of such freeform fields (or even of a radiology report written entirely freeform) in order to identify checklist update triggers such as the imaging modality, medically related image features or a medical diagnosis entered by the radiologist, and so forth.

The workstation 20 includes a communication system supporting the dynamic checklist system 40. The checklist system adapts checklists to the currently available information to support the radiologist at the current stage in the radiology images reading workflow. The checklists propose items for inclusion in the radiology examination report, propose items to be examined as part of the reading, or so forth. Open checklist items which are worked off or do not apply anymore are automatically removed (or, alternatively, marked as completed), when applicable. As an illustrative example, if the dynamic checklist system 40 detects entry in the report of a diagnostic finding, one or more checklist items are added proposing secondary findings that may be made, medical conditions or risk factors that may be investigated to support (or which may controvert) the diagnostic finding, or so forth.

Figure 2:
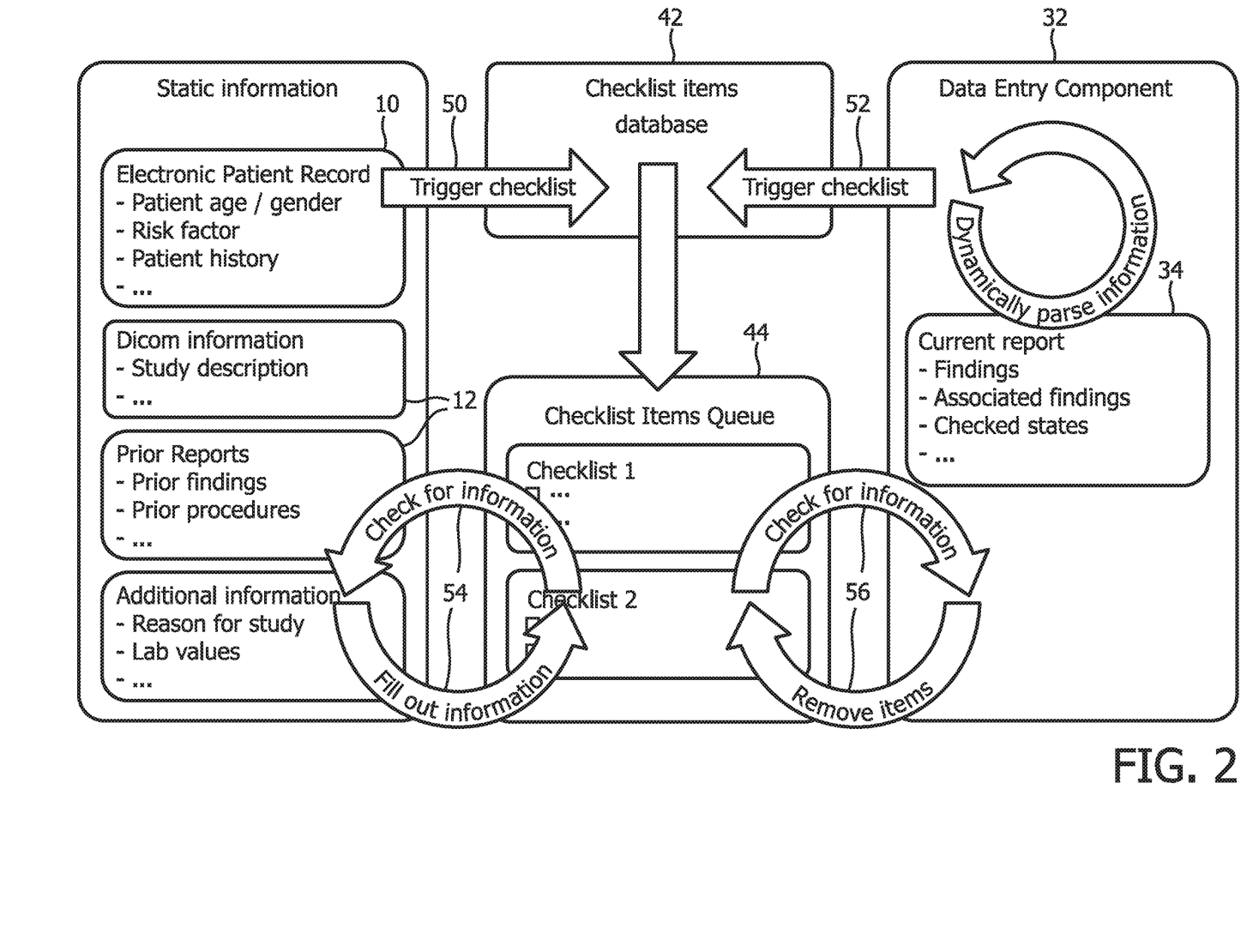
FIG. 2 diagrammatically shows information flow pathways supporting the dynamic checklist system of the radiology workstation of FIG. 1.

With reference to FIG. 2, information flow pathways supporting the dynamic checklist system 40 are diagrammatically shown. The database of checklists 42 can be derived from various sources, such as radiology reporting templates, e.g., available from the RSNA (Radiological Society of North America), or from a large set of previous radiology examinations reports, or generated by expert radiologists (preferably, the checklist items for each examination type or class is generated by a radiologist having especial expertise in that particular type or class). Checklist items may be provided for types of examinations, specific diseases, side effects, risk factors, and so forth. Each checklist item preferably also includes an associated trigger list, that is, information indicating when the checklist item is triggered to be added to the queue 44 of open checklist items. Further, a checklist "item" may comprise a list of items (that is, an entire checklist or "sub-"checklist) for example, a trigger indicating a specific disease may trigger a checklist item comprising an entire checklist of things to check when reading for that disease. The checklist items indicate items to be performed for reporting in a given scenario. This scenario can depend on the type of acquisition, reason for study or current diagnosis. In case of a hypothesized diagnosis, checklist items are suitably included on risk factors (e.g., smoker), laboratory test values (e.g., tumor markers), side effects (e.g., feels better in the morning), and secondary findings or likewise to guide the doctor through his diagnosis.

Communication channels 50, 52 are provided between the database of checklist items 42 (or, the checklist system 40) and static information (channel 50) and dynamic information (channel 52) to enable the dynamic checklist system 40 to trigger checklist items for display when this information meets a checklist item trigger condition. In an embodiment, the initial open checklist items suitably depend on the type of examination (extracted from the dicom metadata associated with the images being read) and provides an initial checklist of which things need to be examined. For example, in a thorax X-ray examination, initially open checklist items may address infiltrations, a pneumothorax, and so forth. Initial checklist items may also be triggered by the reason for study. Checklist items for secondary finding(s) may be triggered by entry of a primary finding into the examination report 34.

Another communication channel 54 is provided to automatically fill checklist items with available information on health status, risk factors or likewise extracted from the static information pool, e.g. from the EMR 10. To this end, a checklist item in the database 42 may be parameterized, and the update of the queue 44 of open checklist items includes identifying a new open checklist item based on an identified checklist update trigger and then retrieving a value for the parameter of the new open checklist item from the EMR archive 10. For example, in a cardiopulmonary radiology examination, a finding of a lung cancer may trigger a checklist item pertaining to whether the patient is a smoker, and the EMR archive 10 is then consulted to retrieve a value for this parameter e.g. "smoker" or "non-smoker" or "past smoker" or so forth. This access to the EMR 10 is preferably done automatically, e.g. using a suitable SQL command or the like, rather than requiring the radiologist to manually navigate the EMR archive 10 using the EMR interface 36 in order to locate this information. In this example, two benefits are gained (1) the radiologist is reminded via addition of the open checklist item that the patient's smoking status should be checked, and (2) the patient's smoking status is automatically provided in the checklist item. Nonetheless, it is not actually entered into the radiology examination report 44 the actual entry of this item would occur only if the radiologist makes the entry into the examination report 44, thus ensuring the radiologist has actually considered the matter and allowing the radiologist to word the entry in a desired manner. In a variant approach, a color indicator or other visualization may be employed to indicate which items support the diagnosis (e.g., the smoking status checklist item may be tagged with a green dot if the status is "smoker" which supports a diagnosis of lung cancer; whereas the smoking status checklist item may be tagged with a red dot if the status is "non-smoker" which does not support a diagnosis of lung cancer).

Another communication channel 56 updates checklist items by removing or fading out (or otherwise marking as completed) a checklist item upon a suitable trigger such as the checklist item being mentioned in the examination report 44. Additionally or alternatively, a checklist item may be removed or marked as completed based upon receipt of a selection of the open checklist item in the display of the checklist via the at least one user input device 24, 26, 28 (for example, the radiologist may click on the item to bring up a dialog box asking if the item has been completed if the radiologist indicates "yes" in that dialog box then the item is removed or marked as completed). This latter approach enables the radiologist to complete an item without mentioning it in the examination report.

As yet another variant, checklist items are optionally marked as "hidden" to yield a less cluttered checklist. In this case, at the end of the radiology examination reporting session conducted on the workstation 20, any remaining hidden items would be again shown to remind the radiologist prior to closing out the session.

To realize these dynamic checklists, the dynamic report analyzer 46 (see FIG. 1) parses the radiology examination report 34 in real-time to detect additions or edits made by the radiologist, and updates the checklist queue 44 to add new open checklist items or to remove (or mark as completed) existing open checklist items based on trigger events detected by the parsing. In a straightforward embodiment, the dynamic report analyzer 46 is keyword-based that is, checklist item addition/removal is triggered by addition of keywords indicating the item should be considered, or has been completed. For example, entry of the term "pulmonary carcinoma" in the examination report 34 triggers the checklist of items relating to lung cancer including the checklist item of whether the patient is a smoker; subsequent entry of "smoker" or "non-smoker" (as appropriate) then triggers removal of (or marking as completed) this checklist item. In other embodiments, the dynamic report analyzer 46 includes a natural language processing (NLP) component including a parser to determine grammatical context of such keywords, and this additional information may be used to more precisely operate the dynamics of the checklist.

Figure 3:
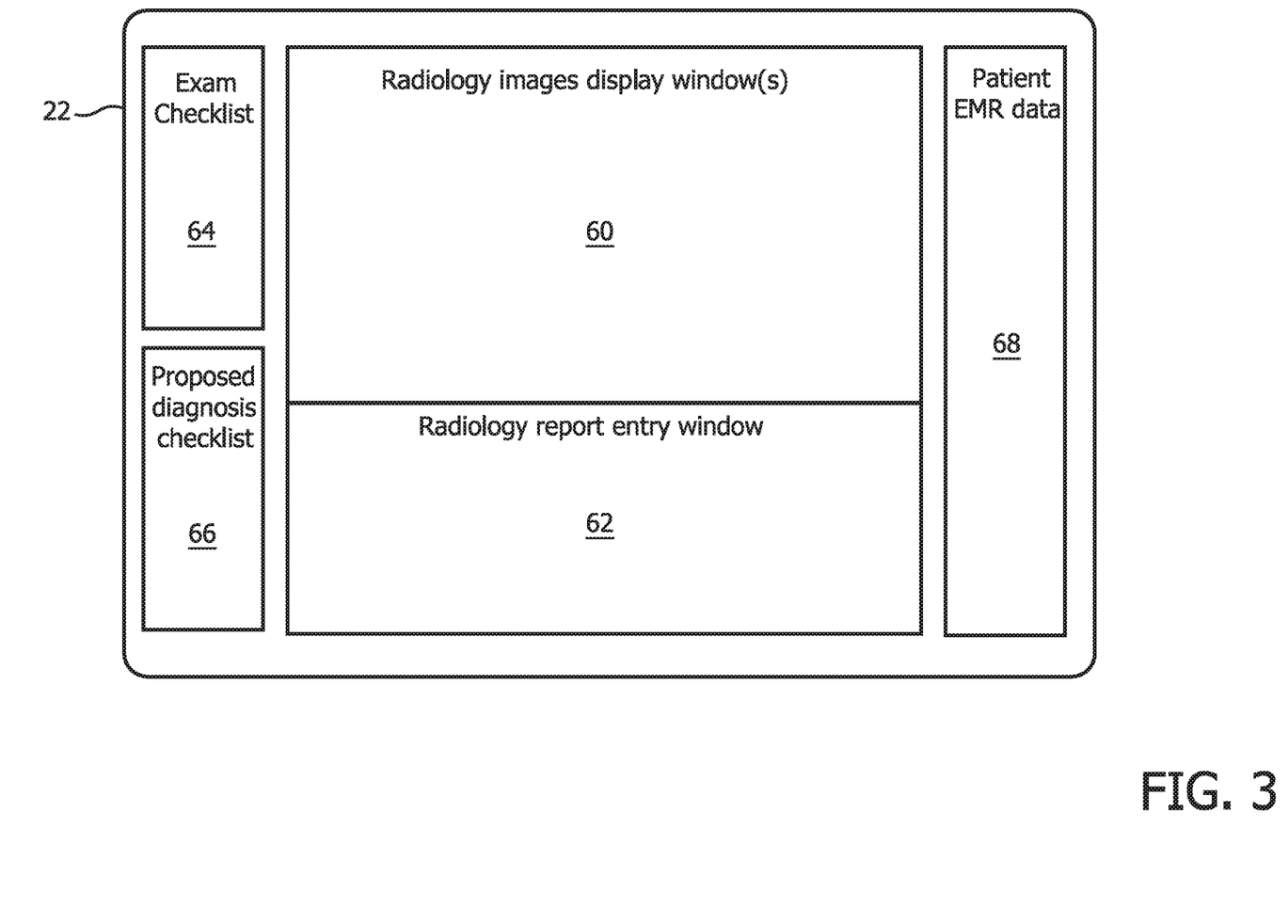
FIG. 3 diagrammatically shows a graphical user interface (GUI) display provided by the radiology workstation of FIG. 1 including dynamic checklists displayed in side windows.

With reference back to FIG. 1 and with further reference to FIG. 3, a graphical user interface (GUI) display suitably shown on the display device 22 includes: a rendering window 60 in which the image rendering component 30 renders radiology images; a radiology report entry window 62 in which the data entry component 32 displays the radiology examination report 34 during entry; one or more (illustrative two) checklist windows 64, 66 displayed on the left side of the main windows 60, 62 which contain (in the illustrative example) an examination checklist and a proposed diagnosis checklist, which are generated by the dynamic checklist system 40; and a patient EMR data window 68 in which the EMR interface 36 displays patient information from the EMR archive 12. The dynamic checklist is intended to be a supplement to the radiologist, and is preferably not imposed upon the radiologist if he or she does not want to use it. In illustrative FIG. 3, this is accomplished by displaying the checklists as side windows 64, 66 that do not impinge upon the main rendering window 60 or upon the report entry window 62. Although not shown, it is contemplated for the checklist windows 64, 66 to include window minimization and/or closure buttons that are selectable by the radiologist using a pointing device 26, 28 to minimize or close these windows to free more screen space for the main windows 60, 62. All windows 60, 62, 64, 66, 68 are optionally resizable so that the radiologist can size and position the windows to personal taste. By displaying the checklist window(s) 64, 66 as separate window(s) from the report entry window 62, the radiologist is reassured that content of the checklists is not being automatically incorporated into the report. The checklist is separate from and not included in the radiology examination report 34, and so providing the checklist(s) in the window(s) 64, 66 does not compromise the radiologist's sole authorship of the contents of the radiology examination report 34. At the same time, the radiologist may optionally manually import material from the checklists into the radiology examination report 34 by manual re-typing, or in some embodiments by drag-and-drop or copy-and-paste operations from the checklist window 64, 66 to the report entry window 62.

In FIG. 3, all windows 60, 62, 64, 66, 68 are shown on a single screen. However, it is contemplated for the display device 22 to include two or more screens. In other words, it is contemplated for the display device 22 to include two or more physical display devices, e.g. two or more LCD monitors or the like. In such cases, it may be advantageous to, for example, use one (preferably highest resolution) LCD monitor to display the rendering window 60, and to use the second (preferably lower resolution) LCD monitor to display the windows 62, 64, 66, 68. In such embodiments, the two or more physical display devices operate in conjunction to implement the display capabilities of the workstation 20, and accordingly as used herein the display device 22 comprises the combination of the two or more physical display devices providing these display capabilities.

Figure 4:
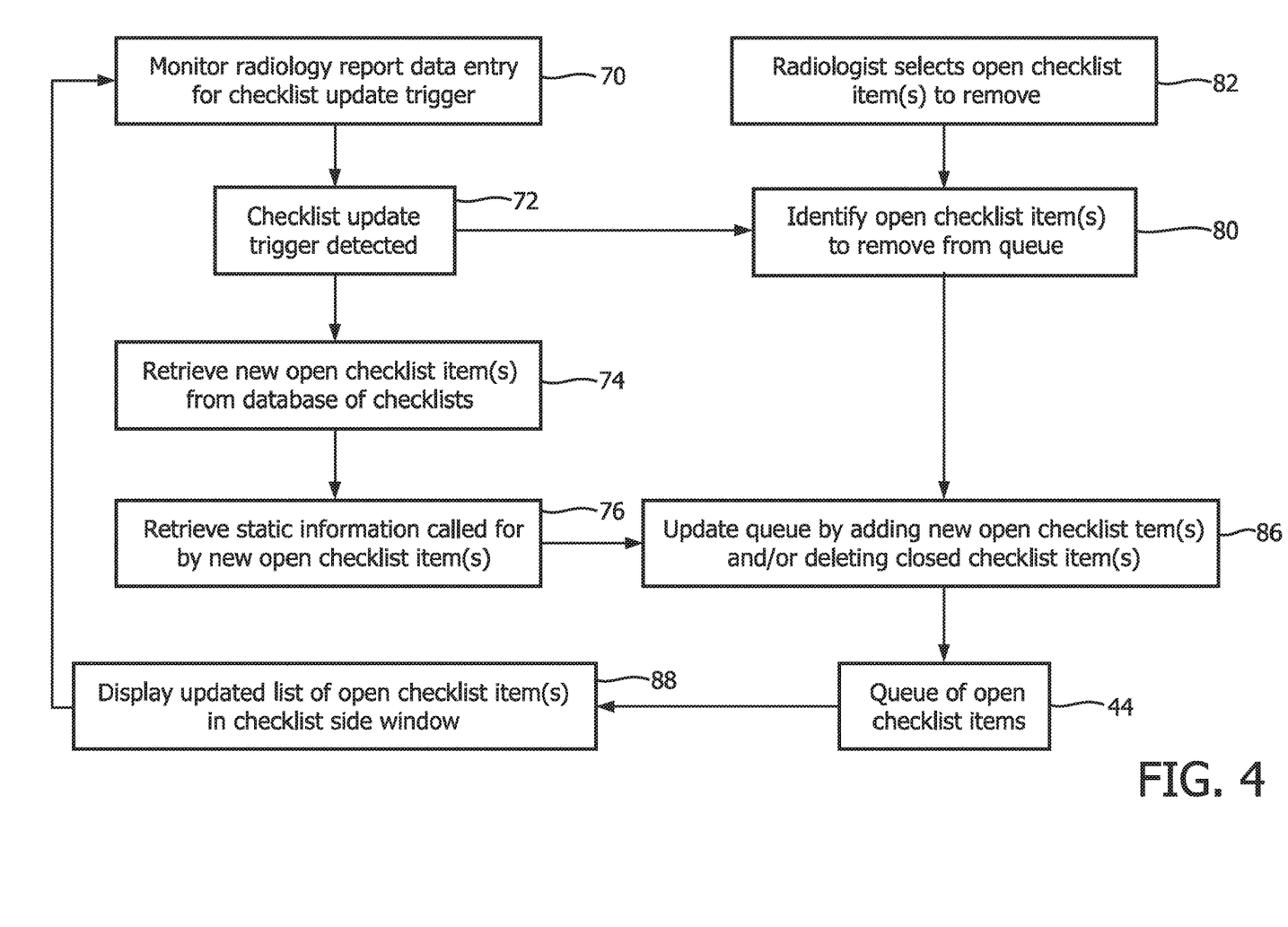
FIG. 4 diagrammatically shows a dynamic checklist update process performed by the dynamic checklist system of the radiology workstation of FIG. 1.

With reference to FIG. 4, a dynamic checklist method suitably performed by the dynamic checklist system 40 of FIG. 1 is described. In an operation 70, it is assumed the initial checklist has been created and displayed, and the radiology examination report entry via the data entry component 32 is monitored for a checklist update trigger. Such a trigger event is detected in a detection operation 72. In an operation 74, the trigger event is compared against the trigger event lists for the checklist items stored in the checklist items database 42 to identify a new open checklist item triggered by the event, and any such event(s) is (are) added to the queue 44. In an operation 76, if the new open checklist item includes any parameters to be filled in (e.g. the smoker status parameter in a checklist item calling for checking whether the patient is a smoker), static information needed to fill in the value of the parameter are retrieved.

If, on the other hand, at the operation 72 it is determined that the trigger event corresponds to closing out an already-open checklist item, then process flow passes to an operation 80 at which the open checklist item(s) to remove (or to mark as completed) are identified. (As noted at operation 82, in some embodiments such items to be removed or marked as completed may alternatively be directly indicated by the radiologist selecting the open checklist item(s) to remove).

In an operation 86, the queue 44 is updated by adding new checklist item(s) generated in operations 74, 76, and/or by removing completed checklist items as per operation 80. In an operation 88 the updated list of open checklist item(s) (that is to say, the updated checklist) is displayed in the checklist window (e.g. in the appropriate one of the windows 64, 66 in the illustrative GUI display of FIG. 3). Processing then returns to operation 70 to await the next occurrence of a trigger event.

After the radiologist has completed the radiology images reading and has completed writing of the radiology examination report 34, the radiology examination report data entry component 32 saves the radiology examination report 34 on a non-transitory storage medium (e.g. on a hard disk, or on a server database such as the PACS 10 and/or the EMR archive 12). On the other hand, the dynamic checklist component 40 discards the content of the queue 44 without saving the checklist. Again, this ensures that the examination report is authored by the radiologist alone, and does not include any content automatically generated by the dynamic checklist system 40. The dynamic checklist component 40 does not add to, delete, or modify the content of the radiology examination report 34. In some embodiments, if there are any remaining open checklist items in the queue 44 when the radiologist acts to close the radiology images reading session, these open checklist items are brought to the radiologist's attention via a suitable dialog window (for example, stating: "The following checklist items have not been completed: [list of open checklist items] . Do you still want to exit?" with suitable selection buttons labeled "Yes" or "No").

It will also be appreciated that the disclosed embodiments of the workstation 20 may be implemented as a non-transitory storage medium storing instructions executable by an electronic data processor to perform embodiments of the radiology examination report generation method as disclosed herein. The non-transitory storage medium may, for example, comprise a hard disk or other magnetic storage medium, a flash memory or other electronic storage medium, an optical disk or other optical storage medium, various combinations thereof, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A radiology workstation comprising:
an image rendering component including a display device and an electronic data processor programmed to render a radiological image on the display device;
a radiology examination report data entry component including the display device, at least one user input device, and the electronic data processor programmed for entry of a radiology examination report via the at least one user input device and display of the radiology examination report on the display device during entry; and
a dynamic checklist component including the display device, a storage medium storing a queue of open checklist items, and the electronic data processor programmed to:
display a checklist on the display device during the entry of the radiology examination report wherein the checklist comprises open checklist items stored in the queue,
dynamically analyze the radiology examination report during the entry of the radiology examination report to identify a checklist update trigger wherein the dynamic analysis of the radiology examination report during entry to identify a checklist update trigger comprises identifying a keyword in the radiology examination report,
update the queue of open checklist items based on the identified checklist update trigger including identifying a new open checklist item based on the identified checklist update trigger and retrieving a value for a parameter of the new open checklist item from an Electronic Medical Record (EMR) archive, and
update the display of the checklist on the display device during the entry of the radiology examination report to comprise the open checklist items stored in the updated queue including displaying the new open checklist item including the retrieved value for the parameter.

2. The radiology workstation of claim 1 wherein:
the update of the queue of open checklist items includes removing or marking as completed an open checklist item from the queue based on the identified checklist update trigger.

3. The radiology workstation of claim 1 wherein the dynamic analysis of the radiology examination report during entry to identify a checklist update trigger comprises parsing the radiology examination report using natural language processing.

4. The radiology workstation of claim 1 wherein the radiology examination report includes one or more freeform entry fields and does not include any constrained user dialog fields.

5. The radiology workstation of claim 1 wherein the display of the checklist on the display device is in a checklist window and the display of the radiology examination report on the display device during entry is in an examination report window different from the checklist window.

6. The radiology workstation of claim 1 wherein the checklist is separate from and not included in the radiology examination report.

7. The radiology workstation of claim 1 wherein the dynamic checklist component does not add to, delete, or modify the content of the radiology examination report.

8. The radiology workstation of claim 1 wherein the radiology examination report data entry component includes the electronic data processor programmed to initialize the radiology examination report to a report form chosen based on a radiological examination order received by the radiology workstation.

9. A radiology examination report generation method comprising:
rendering a radiological image on a display device;
receiving entry of a radiology examination report via at least one user input device, the radiology examination report constituting treatment data for treating a patient who is the subject of the radiology examination report;
displaying the radiology examination report on the display device during entry;
displaying a checklist on the display device comprising open checklist items stored in a queue;
dynamically analyzing the radiology examination report during entry to identify a checklist update trigger;
updating the queue of open checklist items based on the identified checklist update trigger including identifying a new open checklist item based on the identified checklist update trigger and retrieving a value for a parameter of the new open checklist item from an Electronic Medical Record (EMR) archive;
updating the display of the checklist on the display device to comprise the open checklist items stored in the updated queue; and
deleting the open checklist items from the queue after entry of the radiology examination report.

10. The radiology examination report generation method of claim 9 wherein the dynamic analyzing includes at least one of (i) identifying a keyword in the radiology examination report and (ii) parsing the radiology examination report using natural language processing.

11. The radiology examination report generation method of claim 9 wherein:
displaying the radiology examination report comprises displaying the radiology examination report in an examination report window; and
displaying the checklist comprises displaying the checklist in a checklist window different from the examination report window.

12. The radiology examination report generation method of claim 9 further comprising, after entry of the radiology examination report:
saving the radiology examination report on a storage medium; and
discarding the checklist without saving the queue.

13. A non-transitory storage medium storing instructions executable by an electronic data processor to perform a radiology examination report generation method comprising:
rendering a radiological image on a display device in a first window;
receiving entry of a radiology examination report via at least one user input device, the radiology examination report constituting treatment data for treating a patient who is the subject of the radiology examination report;

displaying the radiology examination report on the display device in a second window during entry;

displaying a checklist on the display device in a third window that is different from the second window wherein the checklist comprises open checklist items stored in a queue;

dynamically analyzing the radiology examination report during entry to identify a checklist update trigger;

updating the queue of open checklist items based on the identified checklist update trigger including identifying a new open checklist item based on the identified checklist update trigger and retrieving a value for a parameter of the new open checklist item from an Electronic Medical Record (EMR) archive;

updating the display of the checklist on the display device in the third window to comprise the open checklist items stored in the updated queue; and deleting the open checklist items from the queue after entry of the radiology examination report.

14. The radiology workstation of claim 1, wherein the dynamic checklist component includes the electronic data processor further programmed to:

receive selection of an open checklist item in the display of the checklist via the at least one user input device, and update the queue of open checklist items by removing or marking as completed the selected open checklist item from the queue, and update the display of the checklist on the display device to comprise the open checklist items stored in the updated queue.

15. The radiology workstation of claim 1, wherein, upon completing entry of the radiology examination report:

the radiology examination report data entry component saves the radiology examination report on a storage medium.

16. The radiology examination report generation method of claim 9, wherein:

updating the queue includes removing or marking as completed an open checklist item from the queue based on the identified checklist update trigger.

17. The radiology examination report generation method of claim 9, wherein the receiving entry of a radiology examination report comprises receiving freeform entry and does not include receiving selection of an item via a constrained user dialog field.

* * * * *